United States Patent
Averina et al.

(10) Patent No.: US 9,610,026 B2
(45) Date of Patent: Apr. 4, 2017

(54) METHODS AND APPARATUS FOR DETECTING HEART FAILURE EVENT USING RANK OF THORACIC IMPEDANCE

(71) Applicant: Cardiac Pacemakers, Inc., St. Paul, MN (US)

(72) Inventors: Viktoria A. Averina, Roseville, MN (US); Pramodsingh Hirasingh Thakur, Woodbury, MN (US); Robert J. Sweeney, Woodbury, MN (US); Jonathan Walter Krueger, New Richmond, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 100 days.

(21) Appl. No.: 14/465,362

(22) Filed: Aug. 21, 2014

(65) Prior Publication Data

US 2015/0088026 A1 Mar. 26, 2015

Related U.S. Application Data

(60) Provisional application No. 61/882,866, filed on Sep. 26, 2013.

(51) Int. Cl.
*A61B 5/053* (2006.01)
*A61B 5/00* (2006.01)
*A61B 5/0402* (2006.01)

(52) U.S. Cl.
CPC .......... *A61B 5/0538* (2013.01); *A61B 5/0402* (2013.01); *A61B 5/0537* (2013.01);
(Continued)

(58) Field of Classification Search
CPC ... A61B 5/0402; A61B 5/0538; A61B 5/0537; A61B 5/7275; A61B 5/7282; A61B 5/4878
See application file for complete search history.

(56) References Cited

U.S. PATENT DOCUMENTS 6,572,557 B2 6/2003 Tchou et al.
7,413,549 B1 8/2008 Koh
(Continued)

FOREIGN PATENT DOCUMENTS

EP 1595574 B1 3/2010
WO WO-2015047608 A1 4/2015

OTHER PUBLICATIONS

"International Application Serial No. PCT/US2014/052113, International Preliminary Report on Patentability mailed Apr. 7, 2016", 11 pgs.

(Continued)

*Primary Examiner* — Michael C Stout
(74) *Attorney, Agent, or Firm* — Schwegman Lundberg & Woessner, P.A.

(57) ABSTRACT

Devices and methods for detecting physiological target event such as events indicative of HF decompensation status are described. An ambulatory medical device (AMD) can measure bio-impedance, such as thoracic impedance, from a patient. The AMD can receive a specified threshold within a range or a distribution of impedance measurement, or a specified percentile such as less than $50^{th}$ percentile, and calculate a representative impedance value ($Z_{Rep}$) corresponding to the specified threshold or percentile using a plurality of thoracic impedance measurements. The representative impedance value can be calculated using an adaptation process, or using an estimated distribution of the impedance measurements. The AMD can include a physiologic event detector circuit that can generate a trend of representative impedance values over a specified time period, and to detect a target physiologic event such as indicative of HF decompensation using the trend of representative impedance values.

20 Claims, 9 Drawing Sheets

(52) U.S. Cl.
CPC .......... *A61B 5/4878* (2013.01); *A61B 5/7275* (2013.01); *A61B 5/7282* (2013.01); *A61B 2505/03* (2013.01); *A61B 2505/07* (2013.01)

(56) References Cited

U.S. PATENT DOCUMENTS

| | | | |
|---|---|---|---|
| 7,778,708 B1 | 8/2010 | Koh | |
| 7,986,994 B2* | 7/2011 | Stadler | A61B 5/0537 600/484 |
| 2004/0102712 A1 | 5/2004 | Belalcazar et al. | |
| 2008/0024293 A1* | 1/2008 | Stylos | A61B 5/0537 340/532 |
| 2008/0046019 A1* | 2/2008 | Sathaye | A61N 1/3627 607/28 |
| 2009/0069708 A1* | 3/2009 | Hatlestad | A61B 5/6846 600/547 |
| 2010/0030292 A1* | 2/2010 | Sarkar | A61B 5/053 607/6 |
| 2010/0191076 A1 | 7/2010 | Lewicke et al. | |
| 2011/0098774 A1* | 4/2011 | Brisben | A61N 1/3712 607/28 |
| 2011/0224565 A1 | 9/2011 | Ong et al. | |
| 2011/0230746 A1* | 9/2011 | Jarverud | A61N 1/3627 600/374 |
| 2011/0237968 A1* | 9/2011 | Blomqvist | A61N 1/3627 600/509 |
| 2011/0245711 A1* | 10/2011 | Katra | A61B 5/0537 600/547 |
| 2012/0157874 A1 | 6/2012 | Thakur et al. | |
| 2014/0276151 A1* | 9/2014 | Xi | A61B 5/029 600/508 |

OTHER PUBLICATIONS

"International Application Serial No. PCT/US2014/052113, International Search Report mailed Nov. 24, 2014", 5 pgs.
"International Application Serial No. PCT/US2014/052113, Written Opinion mailed Nov. 24, 2014", 9 pgs.
Gibb, et al., "Algorithms", (Sep. 21, 1961), 321-322.

* cited by examiner

METHODS AND APPARATUS FOR DETECTING HEART FAILURE EVENT USING RANK OF THORACIC IMPEDANCE

CLAIM OF PRIORITY

This application claims the benefit of priority under 35 U.S.C. §119(e) of U.S. Provisional Patent Application Ser. No. 61/882,866, filed on Sep. 26, 2013, which is herein incorporated by reference in its entirety.

TECHNICAL FIELD

This document relates generally to medical devices, and more particularly, to systems, devices and methods for detecting and monitoring events indicative of worsening of congestive heart failure.

BACKGROUND

Congestive heart failure (CHF or HF) is a major health problem and affects over five million people in the United States alone. CHF patients typically have enlarged heart with weakened cardiac muscles, resulting in poor cardiac output of blood. Elevated pulmonary vascular pressures can cause fluid accumulation in the lungs over time. In many CHF patients, fluid accumulation precedes or coincides with episodes of HF decompensation. The HF decompensation can be characterized by pulmonary or peripheral edema, reduced cardiac output, and symptoms such as fatigue, shortness of breath, and the like.

OVERVIEW

Frequent monitoring of CHF patients and timely detection of thoracic fluid accumulation or other events indicative of HF decompensation status can help prevent worsening of HF in CHF patients, hence reducing cost associated with HF hospitalization.

Ambulatory medical devices can be used for monitoring HF patient and detecting HF decompensation events. Examples of such ambulatory medical devices can include implantable medical devices (IMD), subcutaneous medical devices, wearable medical devices or other external medical devices. The ambulatory medical devices can include physiologic sensors which can be configured to sense electrical activity and mechanical function of the heart. The ambulatory medical devices can optionally deliver therapy such as electrical stimulations to target tissues or organs, such as to restore or improve the cardiac function. Some of these devices can provide diagnostic features, such as using transthoracic impedance or other sensor signals to detect a disease or a disease condition. For example, fluid accumulation in the lungs decreases the transthoracic impedance due to the lower resistivity of the fluid than air in the lungs.

Desirable performance of a method or a device for detecting HF decompensation can include one or more of a high sensitivity, a high specificity, or a high positive predictive value (PPV). The sensitivity can be represented as a percentage of actual HF decompensation episodes that are correctly recognized by a detection method. The specificity can be represented as a percentage of actual non-HF decompensation episodes that are correctly recognized as non-HF decompensation events by the detection method. The PPV can be represented as a percentage of the detected HF decompensation episodes, as declared by the detection method, which are actual HF decompensation events. A high sensitivity can help ensure timely intervention to a patient with an impending HF decompensation episode, whereas a high specificity and a high PPV can help avoid unnecessary intervention and added healthcare cost due to false alarms.

HF decompensation detection may be affected by a number of factors including the choice of physiologic sensors or physiologic signals. For example, a detector using a particular sensor signal may provide desirable accuracy in HF decompensation event detection in one patient but less sensitive or less specific in another patient. Additionally, the performance of a detector using one type of sensor signal may change over time such as due to patient's disease progression or development of a new medical condition. Therefore, the present inventors have recognized that there remains a considerable need for improving HF decompensation event detection in CHF patients.

Various embodiments described herein can help improve the detection of target physiologic events such as events indicative of worsening of HF or HF decompensation status. For example, an ambulatory medical device (AMD), such as an implantable medical device or a wearable medical device, can detect an HF decompensation event, such as using one or more representative signal metrics calculated from one or more thoracic impedance signals. The AMD can include an electrical impedance analyzer circuit and a physiologic event detector circuit. The impedance analyzer circuit can measure bio-impedance, such as thoracic impedance, from a patient. The impedance analyzer circuit can receive a specified threshold within a range or a distribution, such as a specified percentile or quartile such as a percentile rank less than $50^{th}$ percentile, and can calculate a representative impedance value ($Z_{Rep}$) corresponding to the specified percentile. The specified percentile can indicate a relative number of a plurality of thoracic impedance measurements with values no greater than the $Z_{Rep}$. The impedance analyzer circuit can calculate the $Z_{Rep}$ using an adaptation process to update the representative impedance value, or using an estimated distribution of the impedance values. The physiologic event detector circuit can generate a trend of representative impedance values over a specified time period, and to detect a target physiologic event using the trend of representative impedance values.

A method for operating a medical device to detect a target physiologic event or condition such as an event indicative of HF decompensation status is also discussed. The method can include measuring bio-impedance from a patient during specified time period. The measured bio-impedance can include a plurality of measurements indicative of thoracic impedance. A specified threshold within a range or a distribution, such as a specified percentile or a quartile such as a percentile rank less than $50^{th}$ percentile, can be received. The method can include generating a representative impedance value ($Z_{Rep}$) corresponding to the specified percentile. The specified percentile can indicate a relative number of the plurality of impedance measurements with values no greater than the $Z_{Rep}$. The method further includes generating a trend of representative impedance values over a specified time period, and using at least the trend of representative impedance values to detect the target physiologic event.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting one or more physiologic target events or conditions. The events can include early precursors of an HF decompensation episode. That is, these events can occur well before the systematic manifestation of worsening of HF. Therefore, by detecting the precursor events, the present subject matter can provide a method and device to detecting an impending HF decompensation episode. In particular, the methods and devices described herein can be applicable to detecting accumulation of thoracic fluid that can forecast an impending HF decompensation episode. More generally, the systems, devices, and methods described herein may be used to determine HF status and/or track HF progression such as worsening of or recovery from an HF event. This system can also be used in the context of other diseases associated with accumulation of thoracic fluid, such as pneumonia.

Figure 1:
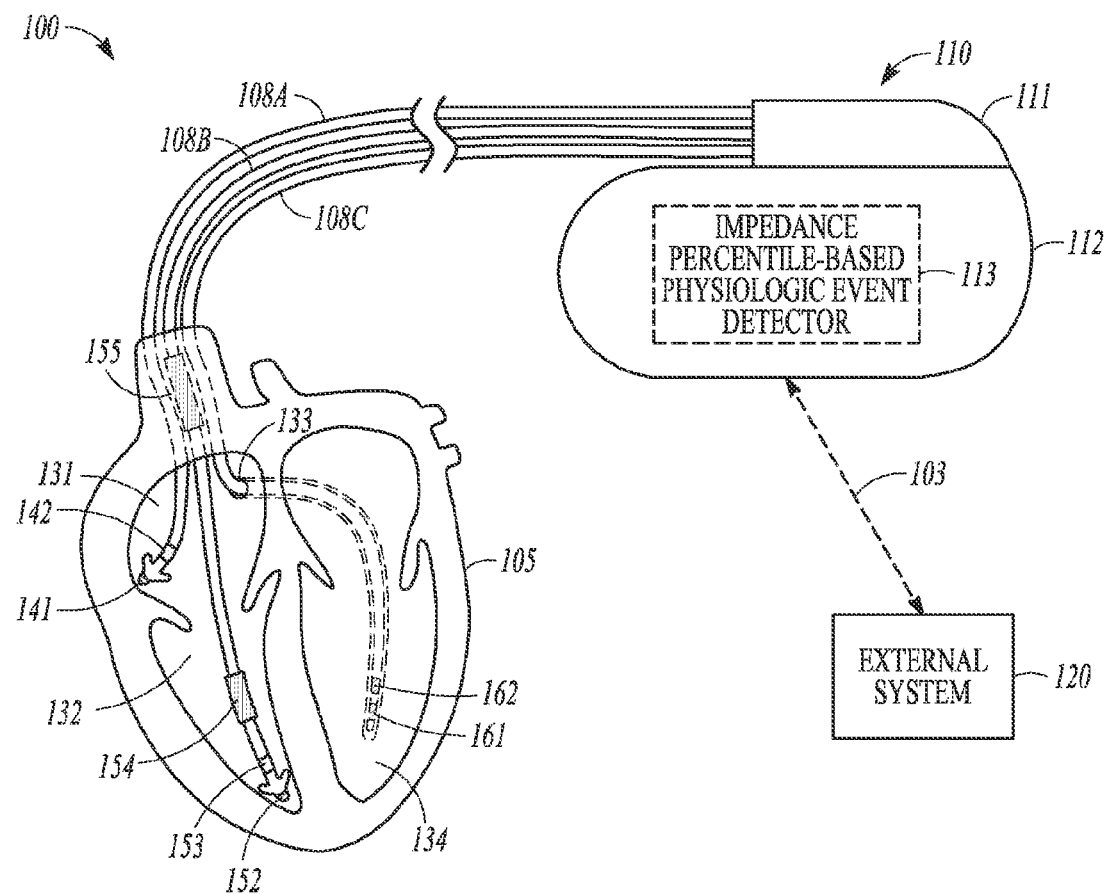
FIG. 1 illustrates an example of a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of thoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are contemplated.

As illustrated, the CRM system 100 can include an impedance percentile-based physiologic event detector 113. The impedance percentile-based physiologic event detector 113 can be configured to receive a physiologic signal indicative of thoracic impedance of a patient. The impedance percentile-based physiologic event detector 113 can also be configured to receive an impedance threshold within a range or a distribution, such as an impedance percentile or quartile such as a percentile rank, of the thoracic impedance. The physiologic signal indicative of the thoracic impedance can be sensed using the electrodes on one or more of the leads 108A-C or the can 112, or other physiologic sensors deployed on or within the patient and communicated with the IMD 110. The impedance percentile-based physiologic event detector 113 can calculate a representative impedance value ($Z_{Rep}$) corresponding to the specified impedance percentile, and detect a target physiologic event or condition of the patient, such as an HF decompensation event, using the representative impedance value $Z_{Rep}$. The HF decompensation event can include one or more early precursors of an HF decompensation episode, or an event indicative of HF progression such as recovery or worsening of HF status. Examples of the impedance percentile-based physiologic event detector 113 are described below, such as with reference to FIGS. 2-4.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The impedance percentile-based physiologic event detector 113 may be implemented in the external system 120. The external system 120 can be configured to perform HF decompensation event detection such as using data extracted from the IMD 110 or data stored in a memory within the external system 120. Portions of the impedance percentile-based physiologic event detector 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
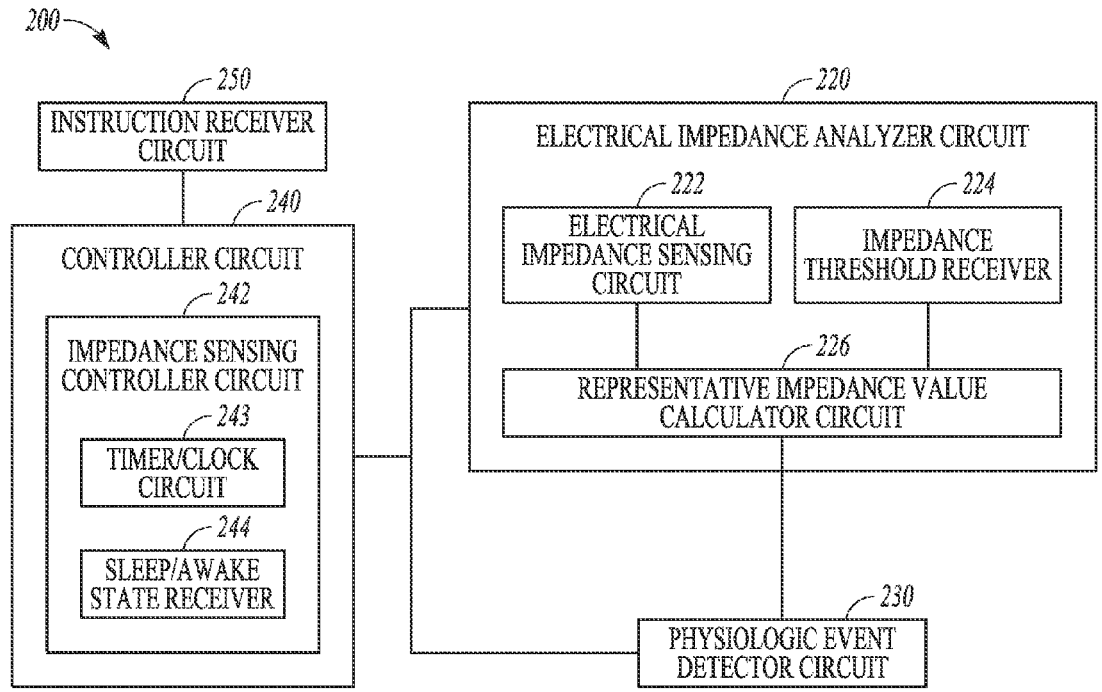
FIG. 2 illustrates an example of a physiologic target event detector based at least on a percentile rank of a thoracic impedance.

FIG. 2 illustrates an example of a physiologic target event detector 200 based at least on an percentile rank of a thoracic impedance measured from a patient. The physiologic target event detector 200 can be an embodiment of the impedance percentile-based physiologic event detector 113. The physiologic target event detector 200 can be configured to detect an event indicative of worsening of heart failure (HF), such as a HF decompensation event. The physiologic target event detector 200 can include one or more of an electrical impedance analyzer circuit 220, a physiologic event detector circuit 230, a controller circuit 240, and an instruction receiver circuit 250.

The electrical impedance analyzer circuit 220 can be configured to sense bio-impedance from a patient and calculate a representative impedance value using the sensed bio-impedance. The electrical impedance analyzer circuit 220 can include an electrical impedance sensing circuit 222, an impedance threshold receiver 224, and a representative impedance value calculator circuit 226. The electrical impedance sensing circuit 222 can be coupled to one or more electrodes on one or more of the leads 108A-C or the can 112, and can be configured to measure bio-impedance from a patient therein. The measured bio-impedance can include a plurality of measurements of thoracic impedance or intracardiac impedance. For example, the bio-impedance can include one or more impedance vectors sensed between an RA electrode 141 or 142 and the can 112 ($Z_{RA\text{-}Can}$), between an RV electrode 152, 153 or 154 and a can 112 ($Z_{RV\text{-}Can}$) or between an LV electrode 161 or 162 and the can 112 ($Z_{RV\text{-}Can}$). The bio-impedance can also include an impedance vector where the voltage sensing electrodes are the currently injection electrodes are orthogonal to each other, such as selected from RA, RV, or LV electrodes ($Z_{RA\text{-}RV\text{-}LV}$). Additionally or alternatively, the electrical impedance sensing circuit 222 can be coupled to one or more implantable or wearable physiologic sensors or one or more patient monitors to sense or receive signals indicative of the bio-impedance thereof.

The electrical impedance sensing circuit 222 can include one or more modules to perform impedance signal conditioning such as signal amplification, digitization, or filtering. The one or more modules can be configured to extract one or more signal metrics from the sensed impedance signal. The signal metrics can include statistical or morphological parameters computed from the sensed impedance signal. Examples of statistical parameters can include signal mean, median, or other central tendency measures, a histogram of the signal intensity, or one or more signal trends over time. Examples of the morphological parameters can include maximum or minimum within a specified period such as a cardiac cycle, positive or negative slope or higher order statistics, signal power spectral density at a specified frequency range, among other morphological descriptors. The impedance signal can be measured at specified time relative to a physiologic event. For example, the impedance can be measured at identical phases of a cardiac cycle (such as within a certain window relative to R-wave) or at identical phases of a respiratory cycle. This may minimize or attenuate the cardiac or respiratory component to the impedance measurements. In some examples, the electrical impedance sensing circuit 222 can sense two or more physiological signals such as two impedance vectors, and can generate a composite signal metric using the two or more physiological signals.

The impedance threshold receiver 224 can be configured to receive a specified threshold within a range or a distribution of impedance measurement, such as a specified impedance percentile, that indicates a relative number of the plurality of the impedance measurements, such as the statistical or morphological signal metrics of the sensed impedance signal, with values no greater than a representative impedance value. In an example, the impedance threshold receiver 224 can receive a specific percentile rank (PR) of the representative impedance value ($Z_{Rep}$). The PR indicates the percentage of the plurality of the impedance measurements that are the same or below the representative impedance value. For example, a 25-th percentile rank of N impedance measurements $\{Z_1, Z_2, \ldots, Z_N\}$ can correspond to a representative impedance value $Z_{Rep}$ where 25% of the N impedance measurements $\{Z_1, Z_2, \ldots, Z_N\}$ are equal to or smaller than $Z_{Rep}$.

The representative impedance value $Z_{Rep}$ corresponding to a PR less than 50% (such as 15%) corresponds to lower impedance value such as during a day, and the $Z_{Rep}$ corresponding to a PR higher than 50% (such as 80%) corresponds to higher impedance value during a day. The higher impedance value such as during a day can happen when the patient is in an upright position or being awake, such that the thoracic fluid that once is accumulated in the thoracic region can be drained away from the thoracic region and redistributed to the rest of the body. In contrast to the belief that larger impedance measured under such conditions may be more sensitive to the events such as HF decompensation, the present inventors have recognized that the lower impedance values such as measured during a day can provide better performance. For example, the lower-quartile portion of an impedance histogram, or the $Z_{Rep}$ corresponding to a PR less than 50%, can be both sensitive and specific to the thoracic fluid status change or events such as HF decompensation. The present inventors have recognized that a subject with an elevated $Z_{Rep}$ corresponding to a lower PR (e.g., 15%) is more likely to develop an HF decompensation event than subject with normal $Z_{Rep}$ corresponding to the lower PR. Thus, $Z_{Rep}$ corresponding to the lower PR can provide a user with enhanced fluid accumulation status information, such as for detecting events indicative of HF decompensation.

The impedance threshold receiver 224 can receive the specified impedance percentile from a user input device capable of allowing an end-user to enter a specific percentile, or to select from a list of pre-set percentiles. For example, the user input device can allow the end-user to enter a percentile rank between 0 and 100% (i.e., $100^{th}$ percentile), or to select one from a list of pre-set percentile rank values between 0 and 100% with an increment of X %. In an example, X can be approximately 1-20%.

The impedance threshold receiver 224 can receive the specified impedance percentile from a memory circuit in which the specified percentile can be pre-stored or programmed. The memory circuit can be configured to store a plurality of impedance percentiles each corresponding to a respective bio-impedance configuration such as an impedance vector. For example, impedance vector $Z_{RA\text{-}Can}$ can be associated with $15^{th}$ percentile, impedance vector $Z_{RV\text{-}Can}$ can be associated with $20^{th}$ percentile, and impedance vector $Z_{LV\text{-}Can}$ can be associated $15^{th}$ percentile. A plurality of impedance percentiles stored in the memory can also be associated with various impedance metrics computed from an impedance signal. For example, for a specific impedance vector such as $Z_{RV\text{-}Can}$, the impedance metric of maximum impedance ($Z_{max}$) can be associated with $20^{th}$ percentile, and impedance metric of steepest slope of the impedance (maxdZ/dt) can be associated with $25^{th}$ percentile. In another example, the impedance values sampled at a specific phases of a cardiac cycle or a respiratory cycle can be associated with $15^{th}$ percentile. The association between the impedance percentiles and the respective impedance configurations or the impedance metrics can be stored in the memory circuit in a data structure such as a look-up table, an association map, or searchable arrays.

The impedance threshold receiver 224 can further be coupled to an impedance vector selector circuit configured to select at least one from the two or more bio-impedance vectors such as sensed by the electrical impedance sensing circuit 222. The impedance threshold receiver 224 can receive from the memory circuit an impedance percentile corresponding to the selected impedance vector, such as by using a look-up table or an association map between the impedance vectors and the corresponding impedance percentile stored in the memory.

The representative impedance value calculator circuit 226 can be coupled to the electrical impedance sensing circuit 222 and the impedance threshold receiver 224. The representative impedance value calculator circuit 226 can be configured to calculate a representative impedance value ($Z_{Rep}$) using the impedance measurements provided by the electrical impedance sensing circuit 222 and the impedance percentile received by the impedance threshold receiver 224. When the received impedance percentile is a percentile rank (e.g., K-th percentile, where 0<K<100), the representative impedance value $Z_{Rep}$ represents an impedance of K-th percentile of the plurality impedance measurements. That is, K % of the impedance measurements provided by the electrical impedance sensing circuit 222 are equal to or less than the impedance measurements representative impedance value $Z_{Rep}$. Examples of determining the $Z_{Rep}$ using the impedance measurements and the received impedance percentile are discussed below, such as with reference to FIGS. 3-5.

The physiologic event detector circuit 230 can receive representative impedance values from the electrical impedance analyzer circuit 220 and be configured to detect a physiologic target event or condition using the representative impedance values. A target event or condition can include a physiologic event indicative of an onset of a disease, worsening of a disease state, or a change of a disease state. In an example, the physiologic event detector circuit 230 can detect the presence of an event indicative of HF decompensation status, worsening HF, pulmonary edema, pneumonia, or myocardial infarction, among others. In some examples, the physiologic event detector circuit 230 can be configured to generate a trend of representative impedance values over a specified time period, and to detect a target physiologic event using at least the trend of representative impedance values.

The controller circuit 240 can control the operations of the electrical impedance analyzer circuit 220 and the subcomponent circuits 222, 224 and 226, the physiologic event detector circuit 230, and the data and instruction flow between these components. The controller circuit 240 can include an impedance-sensing controller circuit 242 that can be configured to control the settings of electrical impedance sensing as used by the electrical impedance sensing circuit 222, where the settings include the electrodes used for current injection and the electrodes used for sensing the resulting voltage. In an example, the impedance-sensing controller circuit 242 can determine an impedance acquisition and analysis session. The impedance acquisition and analysis session can include a time window defined by a specified start and end time, or a specified duration during which the electrical impedance analyzer circuit 220 can sense and analyze the impedance measurements. For example, the impedance-sensing controller circuit 242 can trigger an impedance acquisition and analysis session that starts between approximately 5 a.m. and 9 a.m. in the morning, and lasts for approximately 2-8 hours. In another example, the impedance acquisition and analysis session can be set up to exclude certain time periods, such as night time, or when the patient is asleep.

The impedance-sensing controller circuit 242 can trigger the impedance acquisition and analysis session automatically by a triggering event. Examples of the triggering event include a specific time of a day, a physiologic event such as a change of a physiologic state or a change of the patient's health condition. As illustrated in FIG. 2, the impedance-sensing controller circuit 242 can include one or both of a timer/clock circuit 243 and a sleep/awake state receiver 244 to determine the time and duration of acquiring the impedance measurements. The timer/clock circuit 243 can be programmed to trigger the impedance acquisition and analysis session at a specified time of a day, such as in the morning between 6 a.m. and 12 noon. The timer/clock circuit 243 can also be configured to control the representative impedance value calculator circuit 226 to generate the representative impedance value using a portion of the collected impedance measurements, such as the impedance measurements acquired between 6 a.m. and 12 noon of a day. The electrical impedance analyzer circuit 220 can generate the representative impedance value using impedance measurements acquired during specified duration of the day.

The sleep/awake state receiver 244 can be configured to receive an indication of a change from a sleep state to an awake state. In an example, the sleep/awake state receiver 244 can include a sleep detector configured to detect the transition from sleep to awake state in a patient. The sleep detector can include accelerometers, piezoelectric sensor, biopotential electrodes and sensors, or other physiologic sensors configurable to detect the posture, change of posture, activity, respiration, electroencephalograms, or other physiologic signals indicative of sleep or awake states. In another example, the sleep/awake state receiver 244 can receive indications of a sleep-to-awake state transition from an end-user such as via a user-interface. The received transition from the sleep state to the awake state can be used to trigger the impedance measurement at the electrical impedance sensing circuit 222. Alternatively, the transition to the awake state can be used to control the representative impedance value calculator circuit 226 to generate the representative impedance value using a portion of the plurality of impedance measurements including impedance measurement collected during specified time following the transition to the awake state. The electrical impedance analyzer circuit 220 can generate the representative impedance value using impedance measurements acquired during specified duration from the transition from the sleep to awake state.

The impedance-sensing controller circuit 242 can be configured to receive instructions such as from an end-user regarding the impedance acquisition and analysis session, including start time, end time, or the duration of the session. For example, the impedance-sensing controller circuit 242 can receive external programming input from the instruction receiver circuit 250 to control one or both of the electrical impedance analyzer circuit 220 and the physiologic event detector circuit 230. Examples of the instructions received by the instruction receiver 250 may include: selection of electrodes or sensors used for sensing physiologic signals such as thoracic impedance vectors, selection of timing and duration of the impedance measurement such as via the time/clock 243 or the sleep/awake state receiver 244, or programming of the detection parameters for the physiologic event detector circuit 230. The instruction receiver circuit 250 can include a user interface configured to interactively present programming options to the end-user and to receive user's programming input. In an example, at least a portion of the instruction receiver circuit 250, such as the user interface, can be implemented in the external system 120. The end-user instructions can be programmed to the device memory and retrieved by the impedance-sensing controller circuit 242.

Figure 3:
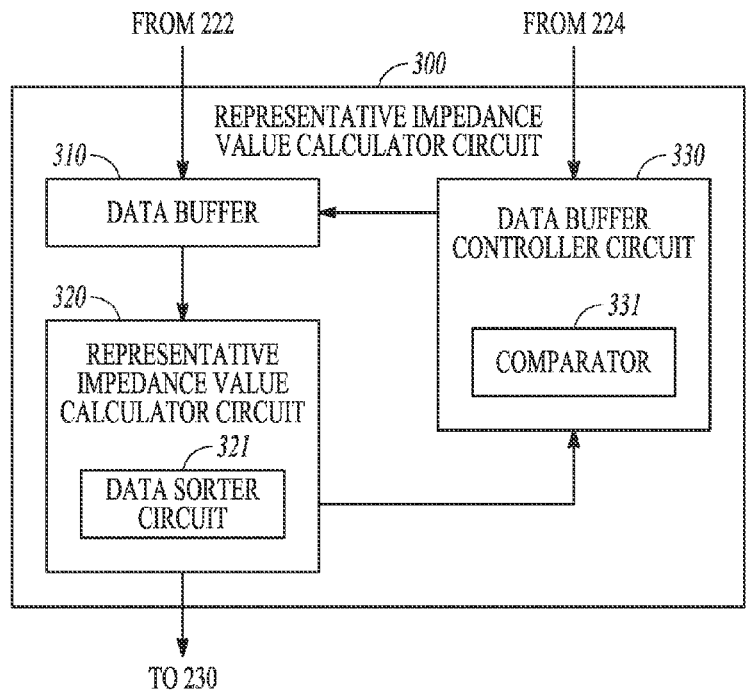
FIG. 3 illustrates an example of the representative impedance value calculator circuit.

FIG. 3 illustrates an example of the representative impedance value calculator circuit 300, as a part of the physiologic target event detector 200. The representative impedance value calculator circuit 300 can be an example of the representative impedance value calculator circuit 226.

The representative impedance value calculator circuit 300 can include a data buffer 310, a representative impedance value calculator circuit 320, and a data buffer controller circuit 330. The data buffer 310 can be configured to receive and store physiologic data such as a plurality of impedance measurements, such as the statistical or morphological impedance metrics generated from the electrical impedance sensing circuit 222.

The data buffer 310 can have a specified buffer size that determines the maximum capacity of the data buffer 310 of receiving the impedance measurements. The buffer size can be determined using a pre-determined number (N) of impedance measurements to be collected (such as using the electrical impedance sensing circuit 222) and a specified impedance percentile (such as received by the impedance threshold receiver 224). The number N can represent total amount of impedance measurements in an impedance acquisition and analysis session as defined by a specified start time, end time, or duration. For example, during an impedance acquisition and analysis session, if the impedance measurements can be generated at a rate R measurements per minute for a time window of T hours, the expected number (N) of impedance measurements in the impedance acquisition and analysis session can be determined as N=R*T*60. When the specified percentile is K-th percentile and K is less than or equal to 50, the buffer size can be at least as large as to receive M=N*K/100=R*T*60*K/100 digitized impedance measurements. If K is greater than 50, then the buffer size can be at least as large as to receive M=N*(100−K)/100=R*T*60*(100−K)/100 digitized impedance measurements.

The impedance acquisition and analysis session can be pre-determined as a time segment of approximately 2-8 hours that starts at approximately 5-9 a.m. in the morning. Additionally or alternatively, the start time of the impedance acquisition and analysis session can be triggered by a physiologic event such as a sleep-to-awake state transition. Parameters that define the impedance acquisition and analysis session can be programmed to the device by an end-user.

The representative impedance value calculator circuit 320 can be configured to calculate a temporary representative impedance value using the impedance values stored in the data buffer 310. The representative impedance value calculator circuit 320 can include a data sorter circuit 321 configured to sort the impedance measurements in the data buffer in descending or ascending order. The representative impedance value calculator circuit 320 can determine the temporary representative impedance value using the sorted impedance values. In an example, the temporary representative impedance value can be determined as the largest value $Z_{max}$ among the impedance measurements stored in the data buffer 310. In another example where the representative impedance value corresponds to a percentile greater than 50, the temporary representative impedance value can be determined as the smallest value $Z_{min}$ among the impedance measurements stored in the data buffer 310.

The data buffer controller circuit 330 can be communicated with the controller circuit 240. In some examples, the data buffer controller circuit 330 can be implemented as a part of the controller circuit 240. The data buffer controller circuit 330 can include a comparator 331 configured to update the impedance data stored in the data buffer 310. The data buffer controller circuit 330 can receive an impedance value Z(n) such as from the electrical impedance sensing circuit 224, and compare Z(n) to the calculated temporary representative impedance value. The comparator 331 can output a control signal for updating the impedance data in the data buffer 310 if the comparison meets a specified condition. In an example where the temporary representative impedance value is $Z_{max}$, if and when the received impedance value Z(n) is smaller than the $Z_{max}$, the impedance data in the data buffer 310 can be updated such that at least $Z_{max}$ can be replaced by the received impedance value Z(n). In another example where the temporary representative impedance value is $Z_{min}$, if and when the received impedance value Z(n) is greater than the $Z_{min}$, the impedance data in the data buffer 310 can be updated such that at least $Z_{min}$ can be replaced by the received impedance value Z(n). The resulting updated impedance values can be received by the representative impedance value calculator circuit 320, where a new temporary representative impedance $Z_{max}$ or $Z_{min}$ can be calculated.

In an example, the data sorter circuit 321 can sort the M impedance measurements in the data buffer 310 in an ascending or descending order. If and when the received impedance value Z(n) is smaller than the $Z_{max}$, Z(n) can be inserted into the sequence of the sorted impedance measurements in the data buffer 310, and the $Z_{max}$ can be removed from the data buffer 310. The data buffer controller circuit 330 maintains the sorted impedance values in the data buffer 310, such that the temporary representative impedance is always the first or the last of the sorted sequence; thereby removing the need for the representative impedance value calculator circuit 320 to calculate the temporary representative impedance (such as $Z_{max}$ or $Z_{min}$) each time when the data buffer 310 has been updated.

If and when the received impedance value Z(n) is equal to or greater than the $Z_{max}$, or equal to or less than $Z_{min}$, the data buffer controller circuit 330 can be configured not to generate a control signal for updating the data buffer 310. As a result, the data buffer 310 is not updated, and the representative impedance value calculator circuit 320 does not recalculate the temporary representative impedance. The data buffer controller circuit 330 can receive next new impedance value Z(n+1) from the electrical impedance sensing circuit 222 and compare it to the temporary representative impedance value $Z_{max}$. The process can be continued until the representative impedance value calculator circuit 300 has processed all N impedance measurements. The resulting temporary representative impedance value ($Z_{max}$ or $Z_{min}$) can be determined as the representative impedance value, which can be passed on to the physiologic event detector circuit 230.

If an impedance acquisition and analysis session terminates prematurely such as interrupted by a pre-determined event or intervened by an end-user, N'(N'<N) impedance measurements have been collected and processed. As a result, $Z_{max}$ of the M impedance measurements in the data buffer 310 constitute K'-th (K'=M/N'*100, where K'>K) percentile rank, rather than the K-th (K=M/N*100) percentile of the N' impedance measurements. To obtain a representative impedance value that represents the K-th percentile among the N' impedance measurements, where K is equal to or less than 50, the representative impedance value calculator circuit 320 can determine the representative impedance value as the N'*K/100-th measurement of the ascending sequence of M impedance measurements in the data buffer 310. Similarly, if K is greater than 50, $Z_{min}$ of the M impedance measurements in the data buffer 310 constitutes the K'-th (K'=(N'−M)/N'*100, where K'<K) percentile rank, rather than the K-th (K=(N−M)/N*100) percentile of the N' impedance measurements. To obtain a representative impedance value that represents the K-th percentile (K>50) among the N' impedance measurements, the representative impedance value calculator circuit 320 can determine the representative impedance value as the N'*(100−K)/100-th measurement of the descending sequence of M impedance measurements in the data buffer 310.

Figure 4:
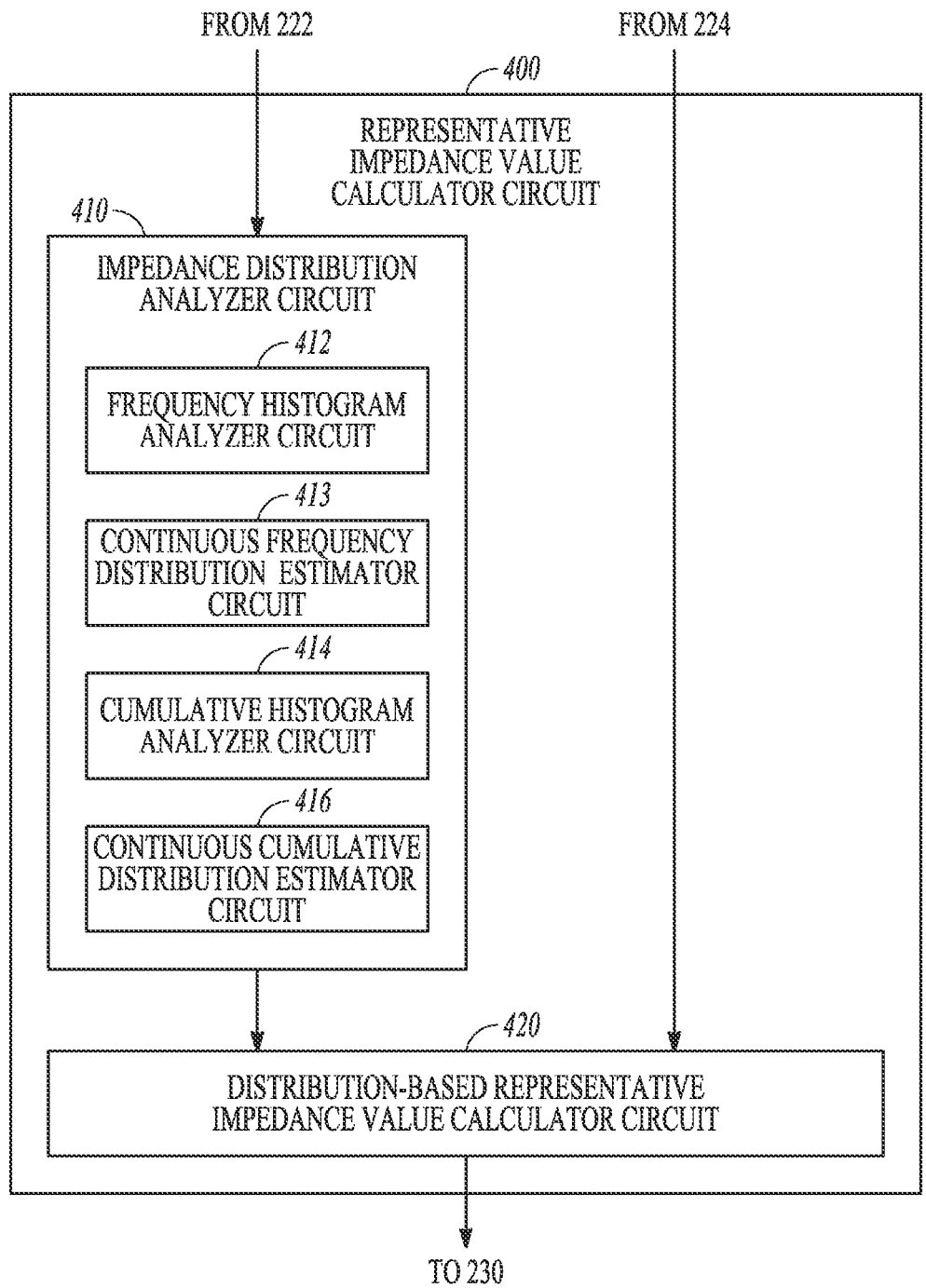
FIG. 4 illustrates another example of the representative impedance value calculator circuit.

FIG. 4 illustrates an example of the representative impedance value calculator circuit 400, as a part of the physiologic target event detector 200. The representative impedance value calculator circuit 400 can be an example of the representative impedance value calculator circuit 226, and can include an impedance distribution analyzer circuit 410 and a distribution-based representative impedance value calculator circuit 420.

The impedance distribution analyzer circuit 410 can be configured to generate an estimate of a statistical distribution of impedance values using the plurality of impedance measurements. The impedance distribution analyzer circuit 410 can include one or more of a frequency histogram analyzer circuit 412, a continuous frequency distribution estimator circuit 413, a cumulative histogram analyzer circuit 414, or a continuous cumulative distribution estimator circuit 416. Each of these analyzer circuits can be adapted to independently generate a statistical distribution estimate.

The frequency histogram analyzer circuit 412 can be configured to generate a histogram representing a distribution of the impedance measurements collected in an impedance acquisition and analysis session. The frequency histogram analyzer circuit 412 can categorize each impedance measurements, such as a value of a statistical or a morphological impedance metric, into one of a specified set of discrete histogram bins. Each histogram bin can be defined by an impedance value range or interval, where the width of the interval determines the bin size. For example, for impedance measurements ranging from 0 to 100 Ohms, ten non-overlapped histogram bins of the same bin size of 10 Ohms can be created, represented by [(k−1)*10, k*10) Ohms, where k=1, 2, . . . , 10. The impedance value range of adjacent histogram bins can be non-overlapped or partially overlapped. The histogram bins can have uniformly identical bin size. Alternatively, at least one bin size is different than at least one another bin size. The frequency histogram analyzer circuit 412 can calculate for each histogram bin a quantity indicating the number of impedance measurements falling with the range of the respective bin. In some examples, the frequency histogram analyzer circuit 412 can calculate for each histogram bin a relative count such as a percentage of the total number of impedance measurements in an impedance acquisition and analysis session.

The continuous frequency distribution estimator circuit 413 can be configured to generate an at least partially continuous frequency distribution of the impedance measurements such as using the impedance measurements collected in an impedance sensing and analysis session. The at least partially continuous frequency distribution can be a mathematical function or a graphical representation of a mapping between a particular impedance value and the frequency of occurrence of the impedance measurements within an infinitesimally small interval of impedance values (dZ) in the neighborhood of a particular impedance value. The continuous frequency distribution estimator circuit 413 can be coupled to the frequency histogram analyzer circuit 412, such that the continuous frequency distribution estimator circuit 413 can generate the frequency distribution using at least a portion of the frequency histogram provided by the frequency histogram analyzer circuit 412.

The cumulative histogram analyzer circuit 414 can be configured to generate a cumulative histogram of the impedance measurements. The cumulative histogram includes, for a specified bin, a cumulative count of impedance measurements in all the histogram bins up to the specified bin. For example, for impedance measurements ranging from 0 to 100 Ohms, ten cumulative histogram bins of the can be created, represented by [0, k*10] Ohms, where k=1, 2, . . . , 10. Each cumulative bin defines an impedance value interval with broader range than any previous cumulative bins. The cumulative histogram analyzer circuit 414 can be coupled to the frequency histogram analyzer circuit 412, such that the cumulative histogram analyzer circuit 414 can generate the cumulative histogram using the frequency histogram from the frequency histogram analyzer circuit 412.

The continuous cumulative distribution estimator circuit 416 can be configured to generate at least a partially continuous cumulative distribution of the impedance measurements such as using the impedance measurements collected in an impedance sensing and analysis session. The at least partially continuous distribution can be a mathematical function or a graphical representation of a mapping between a particular impedance value and the frequency of occurrence of the impedance measurements equal to or less than the particular impedance value. The continuous cumulative distribution estimator circuit 416 can be coupled to the cumulative histogram analyzer circuit 414, and generate the cumulative distribution using at least a portion of the cumulative histogram provided by the cumulative histogram analyzer circuit 414. Alternatively, the continuous cumulative distribution estimator circuit 416 can be coupled to the continuous frequency distribution estimator circuit 413, and generate the cumulative distribution using the estimated continuous frequency distribution provided by the continuous frequency distribution estimator circuit 413. In an example, the continuous cumulative distribution estimator circuit 416 can generate the cumulative distribution by integrating the estimated continuous frequency distribution.

The distribution-based representative impedance value calculator circuit 420 can be configured to determine the $Z_{Rep}$ corresponding to the specified percentile using the estimated statistical distribution such as generated by one or more of the frequency histogram analyzer circuit 412, the continuous frequency distribution estimator circuit 413, the cumulative histogram analyzer circuit 414, or the continuous cumulative distribution estimator circuit 416. Examples of the estimate of the impedance distribution and the representative impedance values determined using the estimated impedance distribution are discussed as follows, such as with reference to FIGS. 5A-C.

Figure 5A:
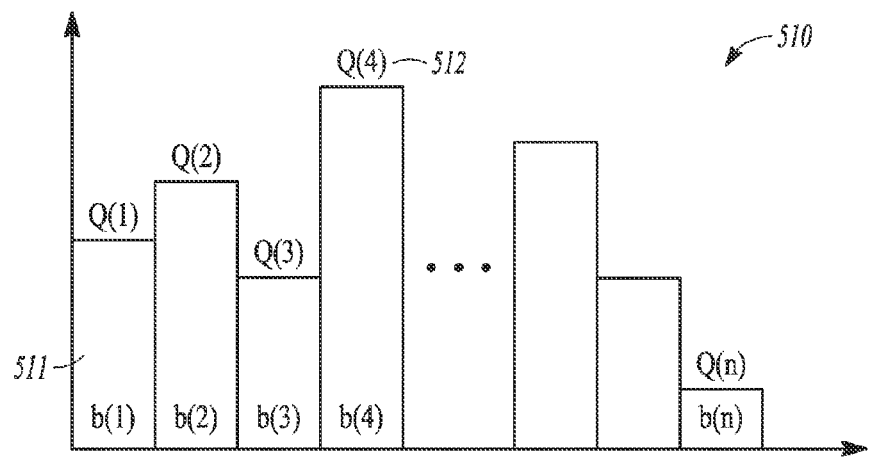
FIGS. 5A-C illustrate various examples of the impedance distribution estimates.
Figure 5B:
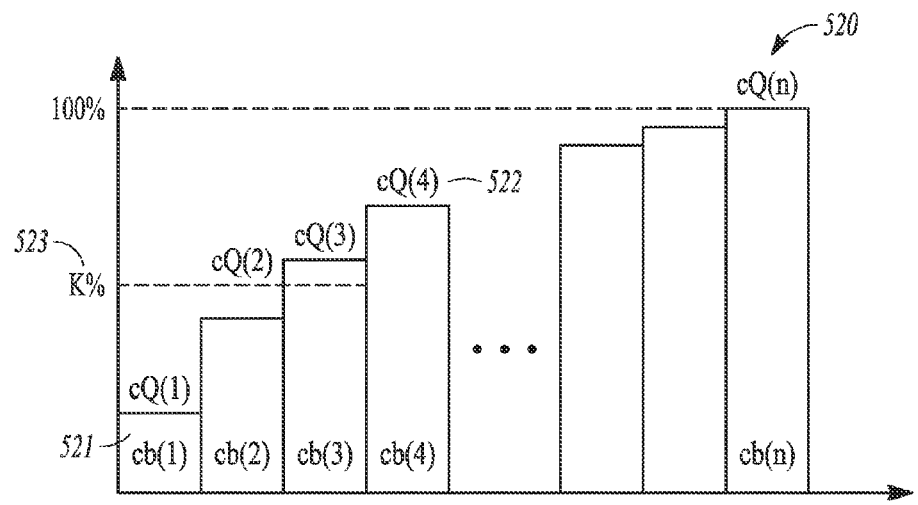
Figure 5C:
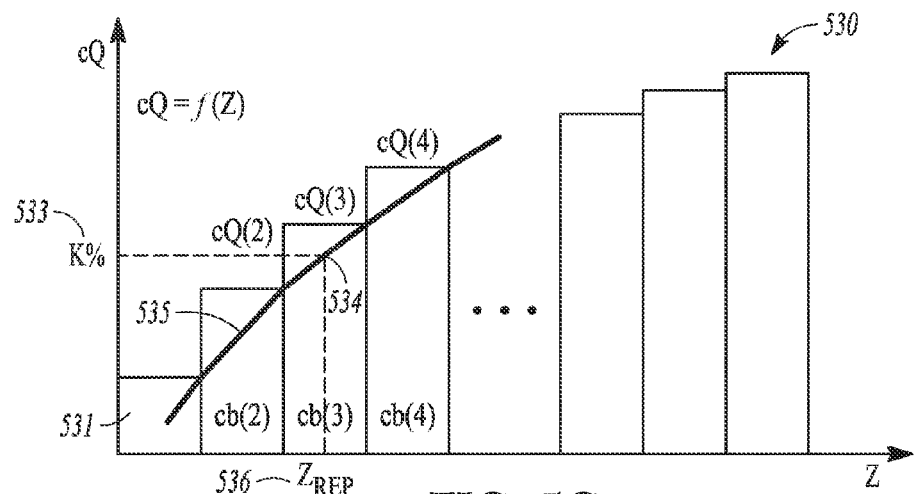

FIGS. 5A-C illustrate various examples of the distribution estimates such as those generated by one or more of the frequency histogram analyzer circuit 412, the cumulative histogram analyzer circuit 414, or the continuous cumulative distribution estimator circuit 416. For example, FIG. 5A illustrates an example of a frequency histogram 510, which can be generated by the frequency histogram analyzer circuit 412. Each impedance value can be categorized into one of a set of non-overlapped bins 511 defined by equally spaced intervals: b(1)=[Z(0), Z(1)), b(2)=[Z(1), Z(2)), b(3)=[Z(2). Z(3)), . . . , b(n)=[Z(n−1), Z(n)], where Z(1)<Z(2)< . . . < Z(n). Each bin b(i) can be associated with a quantity Q(i) 512 representing the percentage of the number of the impedance measurements in an impedance acquisition and analysis session that fall into the impedance range defined by the histogram bin b(i). The K-th percentile of the impedance values in an impedance session can be found as two adjacent cumulative quantities Q(i). That is, $$\Sigma_{i=1}^{n} Q(i) \leq K \leq \Sigma_{i=1}^{n+1} Q(i)$$

For example, if the representative impedance value is chosen to be the 15$^{th}$ percentile rank of impedance measurements in an impedance acquisition and analysis session, and Q(1)=8%, Q2=5%, and Q3=5%, then it can be found that $$Q(1)+Q(2)<15\%<Q(1)+Q(2)+Q(3)$$

That is, the 15$^{th}$ percentile lies between the Q(2) and Q(3). As such, the histogram-based representative impedance value calculator circuit 420 can determine the representative impedance value ($Z_{Rep}$) to be within the impedance range defined by b(3), that is, $Z(2) \leq Z_{Rep} \leq Z(3)$. $Z_{Rep}$ can be determined as the central impedance value $(Z(2)+Z(3))/2$, or as either the lower (Z(2)) or upper bound (Z(3)) of the bin b(3).

In some examples, the $Z_{Rep}$ corresponding to the 15$^{th}$ percentile can be determined using the estimated continuous frequency distribution of the impedance, such as that provided by the continuous frequency distribution estimator circuit 413. For example, an at least partially continuous frequency distribution can be generated within the bin b(3) by interpolating between the boundary impedance values Z(2) and Z(3) using a linear, a piece-wise linear, or a non-linear function. Examples of the nonlinear function can include: polynomial, exponential, power, or logarithmic functions; splines; or radial basis functions. Using the example above, since Q1+Q2=13% and Q1+Q2+Q3=18%, the $Z_{Rep}$ of 15$^{th}$ percentile can be estimated using a linear interpolation between Z(2) and Z(3), that is, $Z_{Rep}=Z(2)+(15-13)/(18-13)*(Z(3)-Z(2))$.

The distribution based representative impedance value calculator circuit 420 can be configured to determine a representative impedance value corresponding to the specified percentile using the generated histogram 510. For example, when the representative impedance value is a K-th percentile rank of the impedance values in an impedance acquisition and analysis session, the histogram-based representative impedance value calculator circuit 420 can determine the representative impedance value by counting and accumulating the quantities of the lower histogram bins, i.e., the histogram bins with lower ranges.

FIG. 5B illustrates an example of a cumulative histogram 520 of the impedance values, which can be generated by the cumulative histogram analyzer circuit 414. The cumulative histogram 520 can be generated using the histogram 510. The cumulative histogram 520 can include a plurality of cumulative bins 521. Each cumulative bin cb(i) can be defined by a range of impedance values wider than the preceding bin cb(i-1). For example, the cumulative bins 521 can be defined by the accumulatively overlapped intervals: cb(1)=[Z(0), Z(1)], b(2)=[Z(0), Z(2)], cb(3)=[Z(0), Z(3)], . . . , cb(n)=[Z(0), Z(n)], where the impedance values Z(i) are constrained by Z(1)<Z(2)< . . . <Z(n). For each cumulative bin, the respective cumulative quantity 522, denoted by cQ(j), can be computed from the quantities Q(i) from all the histogram bins 511 that have the bin intervals falling into the range of the cumulative bin cQ(j). That is, $cQ(j)=\Sigma_{i=1}^{j} Q(i)$.

To determine the representative impedance value corresponding to the specified impedance percentile, the distribution-based representative impedance value calculator circuit 420 can use the cumulative histogram in a fashion similar to the use of the frequency histogram as in FIG. 5A. Because the accumulative histogram establishes the relationship between the cumulative bins (as shown in the x-axis) and the cumulative quantities (as shown in the y-axis), the K-th percentile rank can be determined by finding the cumulative bins with a cumulative quantity K %. As illustrated in FIG. 5B, the cumulative quantity K % at 523 lies between cQ(2) and cQ(3), therefore, the representative impedance value ($Z_{Rep}$) corresponding to the cumulative quantity K % lies between cb(2) and cb(3). Because cb(3) expands the range of cb(2) by incorporating the histogram bin b(3), it can then be determined that the representative impedance value should be within the range defined by b(3), that is, $Z(2) \leq Z_{Rep} \leq Z(3)$. $Z_{Rep}$ can be determined as the central impedance value $(Z(2)+Z(3))/2$, or as either the lower (Z(2)) or upper bound (Z(3)) of the bin b(3).

FIG. 5C illustrates an example of a cumulative distribution curve 535 of the impedance values, which can be generated by the continuous cumulative distribution estimator circuit 416. The cumulative distribution curve 535 includes at least a partially continuous distribution of the impedance measurements collected in an impedance sensing and analysis session. The continuous cumulative distribution estimator circuit 416 can be configured to generate the cumulative distribution curve 535 using the cumulative quantities cQ(i) of two or more cumulative histogram bins. In an example, the histogram analyzer circuit 410 can generate at least a partially continuous distribution using a linear, a piece-wise linear, or a nonlinear curve-fitting of the cumulative quantities cQ(i) of two or more histogram bins cb(i). For example, as illustrated in FIG. 5C, the cumulative distribution curve 535 can be generated by fitting the cQ(2), cQ(3) and cQ(4) to a polynomial function that minimizes the total squared error between the cumulative quantities and the fitted curve. As an alternative to the polynomial function, other nonlinear curving fitting functions can be used, include exponential, power, or logarithmic functions, splines, or radial basis functions. Data interpolation and extrapolation can be used in linear or nonlinear curve-fitting of the cumulative quantities. The fitted at least partially continuous distribution curve 535 can be expressed as $cQ=f(Z)$, where the variable Z (shown on the x-axis) denotes the impedance value, cQ (shown on the y-axis) denotes the relative cumulative quantities such as a percentage of the plurality of impedance measurements with values no greater than Z, and $f$ represents at least a partially continuous linear or nonlinear function. For example, for any given impedance $Z_0$, it can be determined from the fitted distribution curve 535 that among the plurality of impedance measurements, there are $f(Z_0)$ impedance measurements are less than or equal to $Z_0$. That is, $Z_0$ represents a percentile rank of $f(Z_0)*100$.

The distribution-based representative impedance value calculator circuit 420 can be configured to determine the representative impedance value for the specified percentile using the cumulative distribution curve 535. For example, the K-th percentile rank can be equivalent to K % of the relative cumulative quantities. Using the fitted distribution curve 535 which is given by $cQ=f(Z)$, it can be determined that for cQ=K %, the corresponding representative impedance $Z_{Rep}=f^{-1}(K\%)$, where $f^{-1}$ is the inverse of the function $f$. This operation can be illustrated in FIG. 5C, where the corresponding cumulative quantify 533 (K %) can be mapped to $Z_{Rep}$ 536, according to the cumulative distribution curve 535. The point 534 on the cumulative distribution curve 535 corresponds to impedance between cb(2) and cb(3). Because cb(3) expands the range from cb(2) by incorporating the histogram bin b(3), it can then be determined that the representative impedance value should be within the range defined by b(3).

Figure 6:
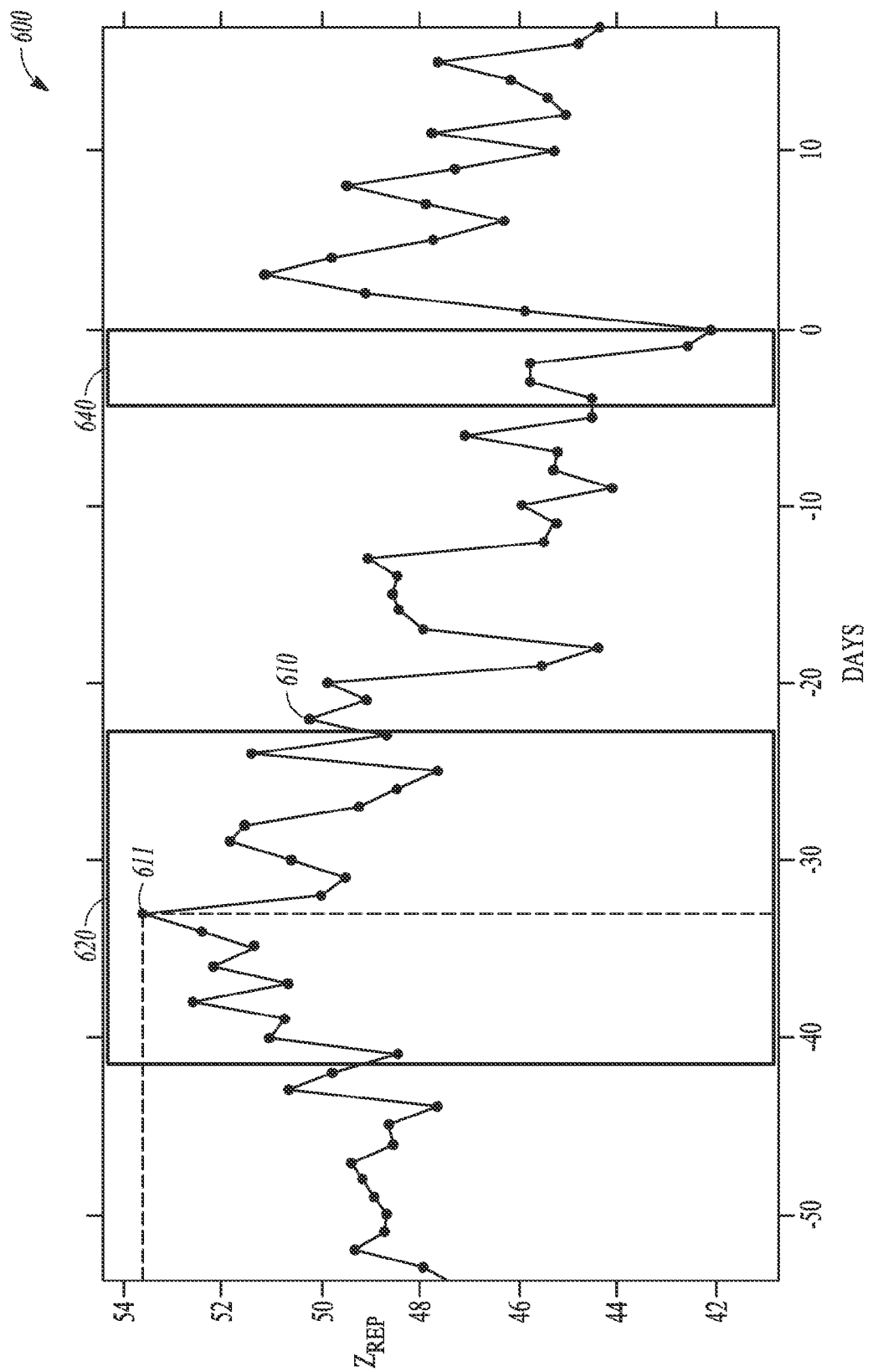
FIG. 6 illustrates an example of a trend of the representative impedance.

FIG. 6 illustrates an example of a trend 600 of the representative impedance $Z_{Rep}$ (as shown in the y-axis)

calculated over a span of approximately 70 days (as shown in the x-axis). The impedance measurements can be acquired by an impedance sensing circuit within an implantable medical device (IMD). The impedance sensing circuit can be configured to couple to one or more electrodes on the RV lead and the IMD housing and to acquire measurements from the RV-Can impedance vector ($Z_{RV-Can}$). Each of the representative impedance values, denoted by data points 610 in the trend 600, represents $15^{th}$ percentile rank among a plurality of impedance measurements acquired during a 24-hour impedance acquisition and analysis session. For example, representative impedance value 611 on the day −33 reaches a peak of approximately 53.5 Ohms, suggesting that 15% of all the $Z_{RV-Can}$ measurements acquired during a 24-hour impedance acquisition and analysis session on day −33 are no greater than 53.5 Ohms. The representative impedance value can be generated by one of the representative impedance value calculator circuits 226, 300, or 400.

A long-term window 620 and a short-term window 640 of the representative impedance values can be specified for use in detecting a target physiologic event, such as worsening of HF or an event indicative of HF decompensation. Statistical measures can be generated respectively using the impedance measurements in the long-term window 620 and the short-term window 640, and a detection decision can be made using a comparison between the statistical measures of the long-term window 620 and the statistical measures of the short-term window 640. Examples of the methods for detecting the target physiologic events using the representative impedance values are discussed below, such as with reference to FIGS. 8-10.

Figure 7:
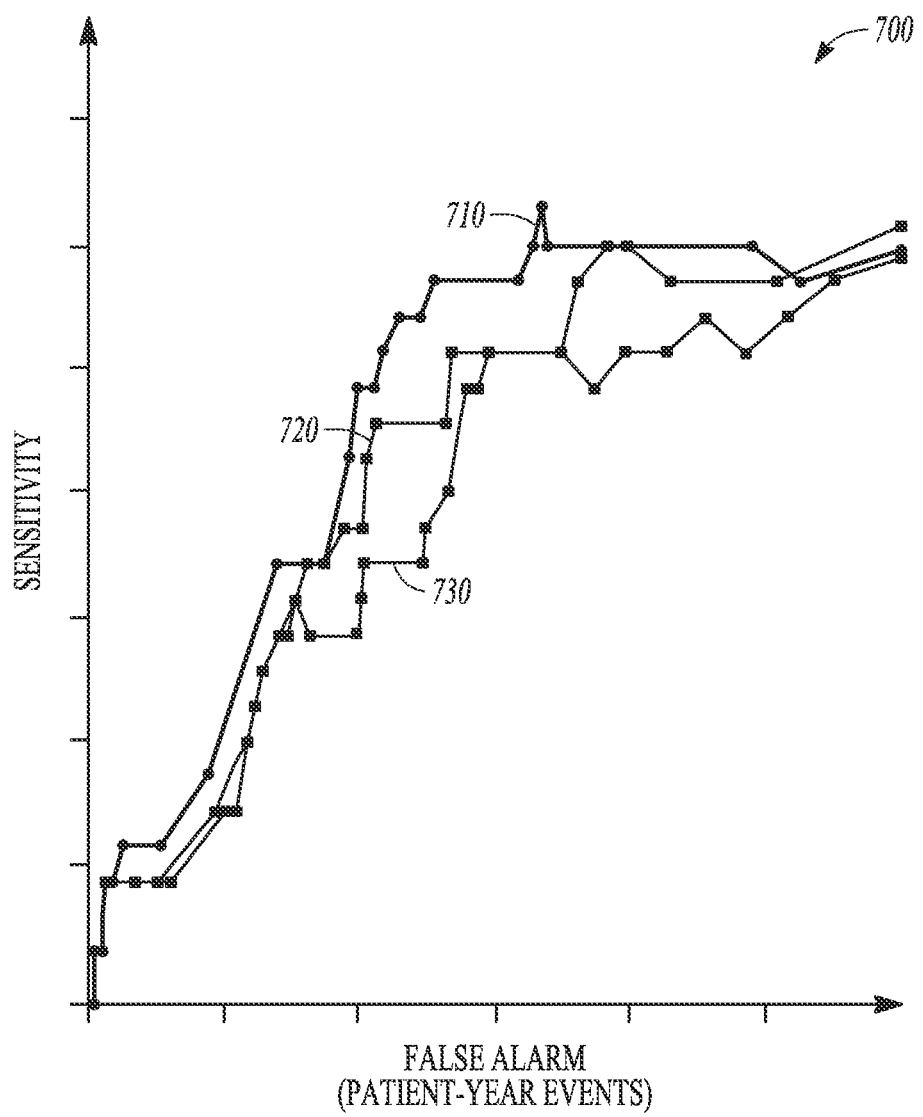
FIG. 7 illustrates an example of receiver operating characteristics (ROC) curves using various representative impedance values.

FIG. 7 illustrates an example of receiver operating characteristics (ROC) curves corresponding to various representative impedance values. In this example, the impedance sensing circuit in the IMD can be configured to acquire impedance measurements from RV-Can vector ($Z_{RV-Can}$). The ROC curves can be used to illustrate and evaluate the performance of a detector or a detection algorithm in detecting the target events indicative of HF decompensation. The ROC curve depicts the sensitivities of detecting the target event (as shown in the y-axis) over the corresponding patient-year false alarm rates (as shown in the x-axis) for a plurality of detection thresholds, such as the threshold for the relative difference between the statistical measures calculated from the short-term window 640 and the statistical measures calculated from the long-term window 620, as illustrated in FIG. 6.

The ROC curves 710, 720 and 730 respectively correspond to daily representative impedance values calculated as the $15^{th}$, $50^{th}$, and $85^{th}$ percentile rank of the impedance measurements acquired over a 24-hour period. FIG. 7 illustrates an example that for a specified false alarm rate, the ROC curve 710 can provide a higher sensitivity than the ROC curves 720 and 730. The area under the ROC curve ($A_{ROC}$), an index that can be used to evaluate a detector's performance, can be computed for the ROC curves 710, 720 and 730. A qualitative comparison also indicates that the $A_{ROC}$ of 710 is larger than the $A_{ROC}$ of 720 and 730. Therefore, in this example, the representative impedance values calculated as the $15^{th}$ percentile rank outperforms the representative impedance values calculated as the $50^{th}$ or $85^{th}$ percentile ranks in detecting events indicative of HF decompensation.

Figure 8:
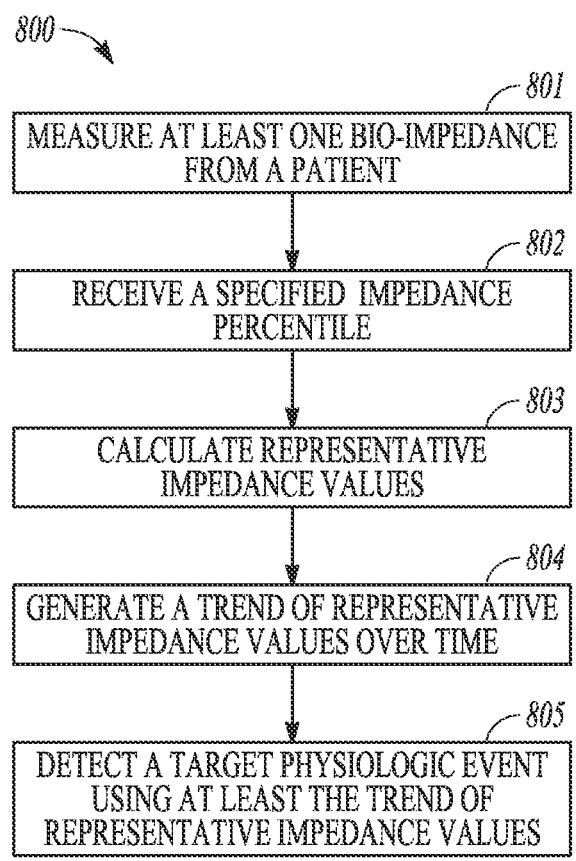
FIG. 8 illustrates an example of a method for detecting a target physiologic event using a physiologic signal.

FIG. 8 illustrates an example of a method 800 for detecting a target physiologic event using a physiologic signal such as a bio-impedance signal. The target physiologic event can include events indicative of worsening of HF or HF decompensation. The method 800 can be implemented and operate in an ambulatory medical device such as an implantable or wearable medical device, or in a remote patient management system. In an example, the method 800 can be performed by the impedance percentile-based physiologic event detector 113 implemented in IMD 110, or the external system 120 in communication with the IMD 110.

At 801, a physiologic signal, such as a bio-impedance signal, can be measured from a patient. The bio-impedance signal can be sensed using one or more electrodes on one or more of the implantable leads such as 108A-C or the can 112 implanted or otherwise attached to the patient. The measured bio-impedance can include a plurality of thoracic impedance measurements or a plurality of intracardiac impedance measurements. The measured bio-impedance can be processed to generate one or more statistical or morphological signal metrics. The bio-impedance signal can be sensed and processed during an impedance acquisition and analysis session. The impedance acquisition and analysis session can include a time duration following a detected physiologic event such as a sleep-to-awake state transition. The impedance acquisition and analysis session can also be determined as a pre-determined time interval of a day, such as a morning between 6 a.m. and 12 noon.

At 802, a specified percentile can be received. The specified impedance percentile can indicate a relative number of the impedance measurements with values no greater than a representative impedance value. An example of the received impedance percentile is a percentile rank (PR) of the representative impedance value ($Z_{Rep}$). The percentile rank, ranging from 0 to 100% (i.e., $100^{th}$ percentile), indicates the percentage of the plurality of the impedance measurements that are no greater than the representative impedance value. In an example, a percentile less than the $50^{th}$ percentile rank is received and used to determine the representative impedance value. The specified impedance percentile can be received from an end-user such as via a user input device, or from a memory that stores pre-determined percentiles. When more than one bio-impedance vectors are selected at 801, various percentiles can be independently chosen for each selected bio-impedance vector at 802.

At 803, a representative impedance value ($Z_{Rep}$) can be calculated using the impedance measurements and the received specified percentile. An estimate of a statistical distribution of impedance values can be calculated from the plurality of impedance measurements. The statistical distribution can be a mathematical function or a graphical representation of a mapping between a particular impedance values and the frequency of occurrence of the impedance measurements equal to or less than the particular impedance value. With a received specified percentile, the corresponding representative impedance value ($Z_{Rep}$) can be found from the estimated statistical distribution.

At 804, a trend of representative impedance values over time can be generated. For example, measurements from a specified impedance vector can be collected in one or more impedance acquisition and analysis sessions, and a representative impedance value can be generated for each session. A first statistical measure can be generated using a first set of representative impedance values calculated during a first time window, and a second statistical measure can be generated using a second set of representative impedance values calculated during a second time window. The first and the second statistical measures can each include a mean, a median, a mode, a percentile, a quartile, or other measures of central tendency among the first or the second set of representative impedance values. In an example, the second time window can be longer than the first window, and at least a portion of the second time window precedes the first time window in time. The second statistical measure computed from the second set of the representative impedance values can be indicative of an impedance baseline ($Z_{Baseline}$). In some examples, the second time window is a moving window and $Z_{Baseline}$ can be adaptively updated such as using a linear combination of the $Z_{Baseline}$ computed from an old window and the impedance values in a new window.

A detection index (DI) can be computed using a comparison between the first and the second statistical measures. The DI represents the trend of impedance value over time, and can indicate presence or severity of a physiologic condition precipitating an HF decompensation episode, such as excessive thoracic fluid accumulation. The DI can be computed as the difference, percentage difference, or other relative difference between the statistical measures from the first short-term window ($Z_{STV}$) and those from the second long-term window ($Z_{Baseline}$). That is, DI=$Z_{Baseline}$−$Z_{STV}$, or DI=($Z_{Baseline}$−$Z_{STV}$)/$Z_{Baseline}$. The DI can also be computed as a rate of change from the second statistical measure ($Z_{Baseline}$) to the first statistical measure ($Z_{STV}$). That is, DI=($Z_{Baseline}$−$Z_{STV}$)/($T_{Baseline}$−$T_{STV}$), where $T_{Baseline}$ and $T_{STV}$ are the representative time for the second and the first time window, respectively.

At 805, a target physiologic event can be detected using at least the trend of representative impedance values. A target event, such as an event indicative of worsening of HF, can be detected if the DI is greater than a threshold. A large DI can thus indicate substantial decrease of representative impedance from the baseline impedance, which can be resulted from an increased thoracic fluid accumulation associated with worsening of HF.

Figure 9:
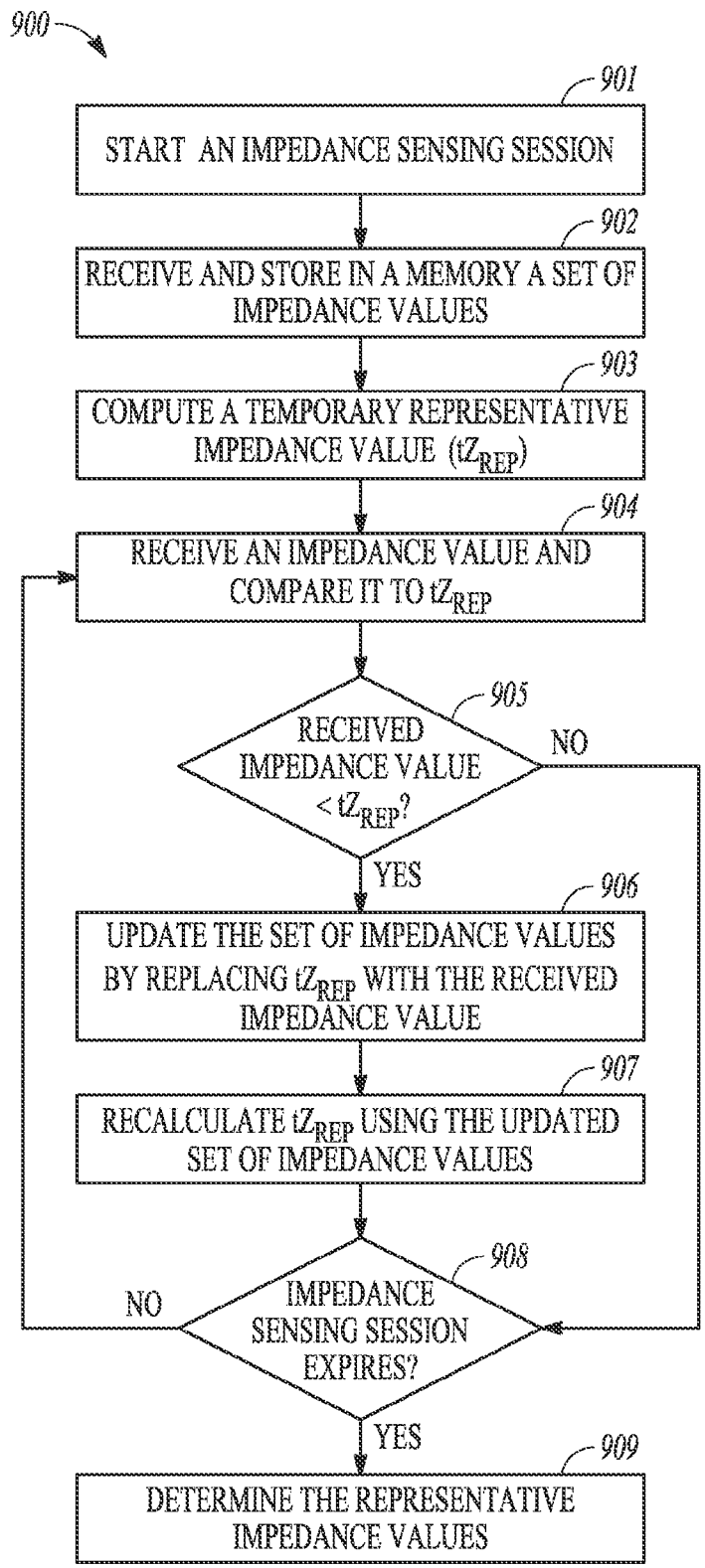
FIG. 9 illustrates an example of a method for calculating a representative impedance value.

FIG. 9 illustrates an example of a method 900 for determining a representative impedance value. The method 900 can be an example of 803 used for detecting a target physiologic event. In an example, the method 900 can be performed by the representative impedance value calculator circuit 226 as illustrated in FIG. 2, or the representative impedance value calculator circuit 300 as illustrated in FIG. 3.

An impedance acquisition and analysis session can be started at 901. The impedance acquisition and analysis session can be triggered by a specified physiologic event and last for a specified duration T, during which the impedance measurements are acquired. The total number N of the impedance measurements that can be collected during the impedance acquisition and analysis session can be determined as N=R*T, where R represents the impedance measurements rate determined by the rate of impedance sampling and impedance metrics calculation.

At 902, a set of impedance values can be received and stored such as in a memory device. The size of the set can be determined using the number of the impedance values in the impedance acquisition and analysis session and the specified percentile. For example, for a K-th percentile, the size of the set can be at least big enough to store N*K/100 impedance measurements. A temporary representative impedance value can then be determined from the set of the impedance values t$Z_{Rep}$ at 903. In an example, the t$Z_{Rep}$ can be determined as the largest value in the set of the impedance values, $Z_{max}$. In some examples, the N*K/100 impedance values can be sorted in an ascending or descending order at 903 for finding the $Z_{max}$.

At 904, a new impedance value Z(n) can be received and compared to the t$Z_{Rep}$. If at 905 the received impedance value Z(n) is less than t$Z_{Rep}$, or a relative difference between the new impedance value and t$Z_{Rep}$ exceeds a threshold value $Z_{TH}$ (e.g., t$Z_{Rep}$−Z(n)>$Z_{TH}$), then the set of impedance measurements can be updated at 906 such as by replacing t$Z_{Rep}$ with Z(n). When the impedance measurements are sorted at 903 in an ascending or descending order, the update can include removing t$Z_{Rep}$ from the set and inserting Z(n) at an appropriate position in the ascending or descending sequence. A new t$Z_{Rep}$ can be calculated using the updated set of impedance values at 907, such as the largest value in the new set.

Following the update of t$Z_{Rep}$ at 907, a session expiration condition is checked at 908. Session expiration condition is also checked if at 905 the received impedance value Z(n) is greater than or equal to the t$Z_{Rep}$, or the relative difference between Z(n) and t$Z_{Rep}$ falls below a threshold value $Z_{TH}$. A session expiration condition can include an indication of the impedance acquisition reaching the end of the duration of the session, total count of impedance values acquired has reached the pre-determined number N, an occurrence of a pre-determined event such as a medical condition of the patient, or an interruption provided by an end-user.

If the session has not expired at 908, then another new impedance measurement Z(n+1) can be received at 904, and the process continues. If the session is determined to be expired at 908, the representative impedance $Z_{Rep}$ can be determined at 909. The representative impedance $Z_{Rep}$ can take the value of t$Z_{Rep}$ if the total count of impedance measurements acquired has reached the pre-determined number N, that is. $Z_{Rep}$=t$Z_{Rep}$. However, if the session expires in response to an occurrence of a pre-determined event or user interruption such that a total of N' (N'<N) impedance measurements are collected and processed, then the N'*K/100-th impedance value in the ascending impedance sequence can be taken as the representative impedance value. The representative impedance value thus determined has the K-th percentile rank among the N' impedance values processed. The calculated $Z_{Rep}$ can then be used to generate a trend of representative impedance values such as at 804 for use in detecting the target physiological event.

Figure 10:
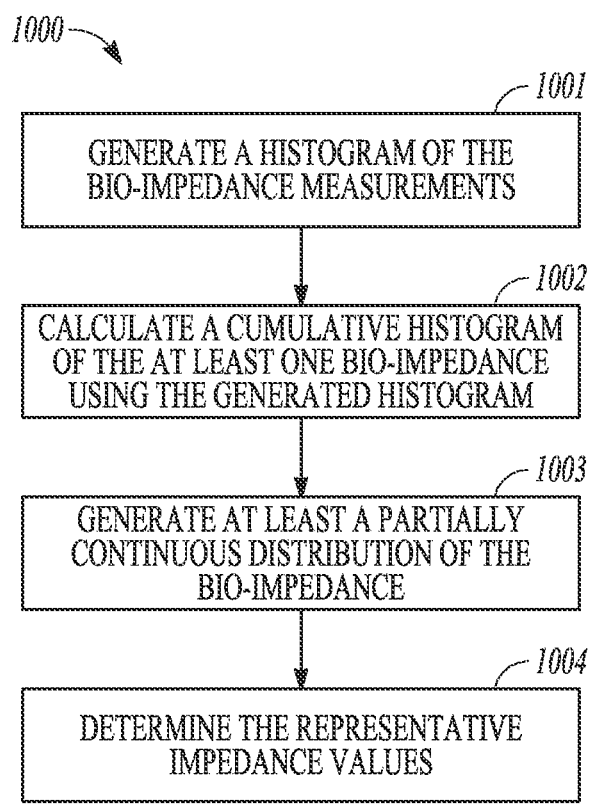
FIG. 10 illustrates an example of a method for calculating a representative impedance value using an estimate of a statistical distribution of impedance measurement.

FIG. 10 illustrates an example of a method 1000 for determining a representative impedance value using an estimate of a statistical distribution of impedance measurement. The method 1000 can be an example of 803 used for detecting a target physiologic event. In an example, the method 1000 can be performed by the representative impedance value calculator circuit 226 as illustrated in FIG. 2, or the representative impedance value calculator circuit 400 as illustrated in FIG. 4.

A histogram of the bio-impedance measurements can be generated at 1001 such as using a plurality of impedance measurements acquired and processed at 801. Each impedance measurement, such as a value of a statistical or a morphological impedance metric, can be categorized into one of a specified set of discrete histogram bins, and a quantity indicating the number of impedance measurements falling into the range of the respective bin can be calculated. The histogram thus generated can represent a distribution of the impedance measurements collected in an impedance acquisition and analysis session.

At 1002, a cumulative histogram of the impedance measurements can be generated using the histogram created at 1001. The cumulative histogram includes, for a specified bin, a cumulative count of impedance measurements in all of the histogram bins up to the specified bin. Each cumulative bin defines an impedance value interval with broader range than any of its previous cumulative bins. The cumulative histogram can thus be seen as accumulation of the bins in the histogram.

At 1003, a cumulative distribution function of the impedance can be estimated. The cumulative distribution function can include at least a partially continuous distribution function such as using two or more cumulative bins of the cumulative histogram. The at least partially continuous distribution can be generated using a linear, a piece-wise linear, or a nonlinear curve-fitting of two or more cumulative histogram bins. The at least partially continuous distribution can be expressed as a mathematical function $cQ=f(Z)$, where Z denotes the impedance value, cQ the relative cumulative quantities (such as a percentage of the plurality of impedance measurements) with values no greater than Z, and $f$ a linear or a nonlinear function establishing a mapping between a particular impedance value and the frequency of occurrence of the impedance values equal to or less than the particular impedance value. The at least partially continuous distribution can also be represented by a graphical distribution curve, such as illustrated in FIG. 5C.

At 1004, the representative impedance value corresponding to the specified percentile (e.g., K-th percentile rank) can be determined using the at least partially continuous cumulative distribution function or the distribution curve. For example, the K-th percentile rank received at 802 can be equivalent to K % of the relative cumulative quantities, that is, cQ=K %. Using distribution function $cQ=f(Z)$, the representative impedance value can be calculated as $Z_{Rep}=f^{-1}(K\%)$, where $f^{-1}$ is the inverse of the function $f$. The calculated $Z_{Rep}$ can then be used to generate a trend of representative impedance values such as at 804 for use in detecting target physiological event.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
an ambulatory medical device (AMD), including:
an electrical impedance analyzer circuit, comprising:
an electrical impedance sensing circuit configured to measure bio-impedance from a patient, the bio-impedance including a plurality of thoracic impedance measurements indicative of a thoracic fluid status; and
a representative impedance value calculator circuit configured to calculate, from the measured bio-impedance, a representative impedance value ($Z_{Rep}$) corresponding to a predetermined threshold associated with a statistical distribution of the measured bio-impedance, wherein the statistical distribution indicates frequencies of occurrence of the plurality of thoracic impedance measurements, and the predetermined threshold indicates a relative number, greater than zero and less than 50%, of the plurality of thoracic impedance measurements with values no greater than the $Z_{Rep}$; and
a physiologic event detector circuit configured to generate a heart failure detection index indicating a diagnostic of worsening heart failure using the representative impedance value.

2. The system of claim 1, wherein the electrical impedance analyzer circuit includes an impedance threshold receiver configured to receive the predetermined threshold including a percentile rank less than $50^{th}$ percentile of the plurality of thoracic impedance measurements.

3. The system of claim 1, wherein the AMID comprises:
a memory circuit configured to store two or more impedance thresholds for respective two or more bio-impedance vectors different from each other; and
an impedance vector selector circuit configured to select at least one from the two or more bio-impedance vectors, wherein the electrical impedance analyzer circuit includes an impedance threshold receiver, coupled to the memory circuit, configured to receive from the memory circuit a respective threshold for the selected bio-impedance vector, and wherein the representative impedance value calculator circuit is configured to calculate a representative impedance value for the selected bio-impedance vector using the respective threshold.

4. The system of claim 1, wherein the physiologic event detector circuit is configured to generate a trend of representative impedance values over a specified time period, and to generate the heart failure detection index using the trend of representative impedance values.

5. The system of claim 1, wherein:
the AMD includes an implantable cardiac device; and
wherein the electrical impedance sensing circuit is configured to measure the bio-impedance including intra-thoracic impedance using two or more electrodes coupled to the electrical impedance sensing circuit, the two or more electrodes including a can electrode electrically tied to a housing of the implantable cardiac device.

6. The system of claim 1, wherein the representative impedance value calculator circuit comprises:
a data buffer circuit with specified buffer size, the data buffer circuit configured to receive and store a plurality of impedance measurements from the electrical impedance sensing circuit, the specified buffer size determined using a total number of impedance measurements to be collected within specified time period by the electrical impedance sensing circuit and the predetermined threshold;
a representative impedance value calculation circuit configured to determine a temporary representative impedance value using the impedance measurements stored in the data buffer circuit; and
a data buffer controller circuit, including a comparator configured to receive an impedance measurement from the electrical impedance sensing circuit and compare it to the temporary representative impedance value, wherein the controller is configured to update the impedance measurements stored in the data buffer circuit using a comparison between the received impedance measurement and the temporary representative impedance value.

7. The system of claim 1, wherein the representative impedance value calculator circuit comprises:
an impedance distribution analyzer circuit configured to generate an estimate of a statistical distribution of impedance values using the plurality of impedance measurements; and
a distribution-based representative impedance value calculator circuit configured to determine the representative impedance value using the estimate of statistical distribution of impedance values and the predetermined threshold.

8. The system of claim 7, wherein the impedance distribution analyzer circuit includes a frequency histogram analyzer circuit configured to categorize the plurality of impedance measurements each into one of a specified set of discrete histogram bins, and to calculate a relative count of the impedance measurements inside respective bin, each histogram bin defined by an impedance value range.

9. The system of claim 7, wherein the impedance distribution analyzer circuit includes a cumulative histogram analyzer circuit configured to generate a cumulative histogram of the bio-impedance values, the cumulative histogram including, for a specified bin, a cumulative count of impedance measurements in all of the histogram bins up to the specified bin.

10. The system of claim 7, wherein impedance distribution analyzer circuit includes at least one of a continuous frequency distribution estimator circuit or a continuous cumulative distribution estimator circuit, the continuous frequency distribution estimator circuit configured to generate at least a partially continuous distribution of the bio-impedance using quantities in two or more histogram bins, the continuous cumulative distribution estimator circuit configured to generate at least a partially continuous distribution of the bio-impedance using cumulative quantities in two or more cumulative histogram bins.

11. The system of claim 10, wherein the histogram analyzer circuit is configured to generate at least the partially continuous distribution using linear or nonlinear interpolation of the cumulative quantities in two or more histogram bins.

12. The system of claim 1, wherein the electrical impedance analyzer circuit is configured to generate the representative impedance value using a portion of the plurality of impedance measurements including impedance measurements collected during a morning of a day.

13. The system of claim 1, further comprising a sleep state detector configured to detect a time of transition from a sleep state to an awake state, wherein the electrical impedance analyzer circuit is configured to generate the representative impedance value using impedance measurements collected after the transition from the sleep state to the awake state.

14. A method, comprising:
measuring bio-impedance from a patient, via an ambulatory medical device (AMD), during a specified time period, the bio-impedance including a plurality of thoracic impedance measurements indicative of a thoracic fluid status;
generating, from the measured bio-impedance, a representative impedance value ($Z_{Rep}$) corresponding to a predetermined threshold associated with a statistical distribution of the measured bio-impedance using a representative impedance value calculator circuit, wherein the statistical distribution indicates frequencies of occurrence of the plurality of thoracic impedance measurements, and the predetermined threshold indicates a relative number, greater than zero and less than 50% of the plurality of thoracic impedance measurements with values no greater than the $Z_{Rep}$; and
generating, using physiologic event detector circuit, a heart failure detection index indicating a diagnostic of worsening heart failure using the representative impedance value.

15. The method of claim 14, including:
generating a trend of representative impedance values, including:
  calculating a first impedance statistic using a first set of representative impedance values calculated during a first time window; and
  calculating a second impedance statistic using a second set of representative impedance values calculated during a second time window, the second impedance statistic indicative of a baseline of impedance; and at least a portion of the second time window preceding the first time window; and
wherein generating the heart failure detection index includes determining a comparison of the first impedance statistic and the second impedance statistic meeting a specified criterion.

16. The method of claim 15, wherein:
generating the first impedance statistic includes generating a first central tendency of the first set of the representative impedance values; and
generating the second impedance statistic includes generating a second central tendency of the second set of the representative impedance values and adaptively updating the second central tendency.

17. The method of claim 14, wherein the predetermined threshold includes a percentile rank less than $50^{th}$ percentile of the thoracic impedance measurements.

18. The method of claim 14, wherein generating a representative impedance value includes:
receiving and storing in a memory a plurality of impedance values of specified size, the size determined using a desired number of impedance values to be collected by the electrical impedance and the predetermined threshold;
computing a temporary representative impedance value using the plurality of impedance values; and
receiving an impedance value and comparing it to the temporary representative impedance value;
updating the plurality of the impedance values in the memory using the comparison between the received impedance value and the temporary representative impedance value;
updating the temporary representative impedance value using the updated plurality of impedance values; and
determining the representative impedance value using the updated temporary representative impedance value in response to a specified session expiration condition being met.

19. The method of claim 14, wherein generating a representative impedance value includes:
generating a frequency histogram of the bio-impedance values, the frequency histogram includes a specified set of discrete histogram bins each defined by an impedance value range, and a relative count of the impedance measurements inside respective bin;
calculating a cumulative histogram of the bio-impedance values using the frequency histogram, the cumulative histogram including; for a specified bin, a cumulative count of impedance measurements in all of the histogram bins up to the specified bin; and
determining the $Z_{Rep}$ corresponding to the predetermined threshold using the cumulative histogram.

20. The method of claim 14, wherein generating a representative impedance value includes:
generating at least a partially continuous distribution of the bio-impedance using the plurality of impedance measurements; and
determining the $Z_{Rep}$ corresponding to the predetermined threshold using the at least partially continuous distribution of the bio-impedance.

* * * * *